United States Patent
Pugh et al.

(10) Patent No.: US 10,059,790 B2
(45) Date of Patent: Aug. 28, 2018

(54) SYNTHESIS OF CROSS-LINKED PLANT-OIL BASED POLYMERS USING BISMALEIMIDES AS CROSSLINKERS

(71) Applicants: Coleen Pugh, Akron, OH (US); Paula Watt, Ashtabula, OH (US); Brinda Mehta, Cuyahoga Falls, OH (US)

(72) Inventors: Coleen Pugh, Akron, OH (US); Paula Watt, Ashtabula, OH (US); Brinda Mehta, Cuyahoga Falls, OH (US)

(73) Assignee: The University of Akron, Akron, OH (US)

(*) Notice: Subject to any disclaimer, the term of this patent is extended or adjusted under 35 U.S.C. 154(b) by 83 days.

(21) Appl. No.: 14/916,625

(22) PCT Filed: Sep. 5, 2014

(86) PCT No.: PCT/US2014/054280
§ 371 (c)(1),
(2) Date: Mar. 4, 2016

(87) PCT Pub. No.: WO2015/035156
PCT Pub. Date: Mar. 12, 2015

(65) Prior Publication Data
US 2016/0208036 A1    Jul. 21, 2016

Related U.S. Application Data

(60) Provisional application No. 61/874,031, filed on Sep. 5, 2013.

(51) Int. Cl.
  *C08F 2/02*   (2006.01)
  *C08F 2/60*   (2006.01)
  *C08F 222/40* (2006.01)
  (Continued)

(52) U.S. Cl.
  CPC ............ *C08F 222/40* (2013.01); *B01J 31/06* (2013.01); *C07D 207/452* (2013.01);
  (Continued)

(58) Field of Classification Search
None
See application file for complete search history.

(56) References Cited

U.S. PATENT DOCUMENTS 5,817,744 A   10/1998  Sheppard et al.
6,121,398 A   9/2000   Wool et al.
(Continued)

OTHER PUBLICATIONS

Shibata et al. (Journal of Applied Polymer Science, 2011, 119, 896-901).*

(Continued)

*Primary Examiner* — Vu A Nguyen
(74) *Attorney, Agent, or Firm* — Renner Kenner Greive Bobak Taylor & Weber

(57) ABSTRACT

A method of preparing a plant oil based polymer comprising heating a plant oil in the presence of a bismaleimide crosslinker in the substantial absence of a solvent at a temperature at or above the melting temperature of the bismaleimide crosslinker, where the bismaleimide crosslinker is defined by the formula

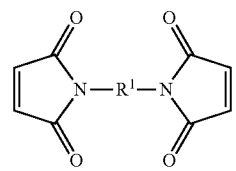

where $R^1$ is a divalent organic group.

14 Claims, 3 Drawing Sheets

(51) Int. Cl.
    *C08F 242/00*     (2006.01)
    *C07D 207/452*     (2006.01)
    *C07D 403/12*     (2006.01)
    *C07D 403/10*     (2006.01)
    *C07D 487/04*     (2006.01)
    *B01J 31/06*     (2006.01)

(52) U.S. Cl.
    CPC ......... *C07D 403/10* (2013.01); *C07D 403/12* (2013.01); *C07D 487/04* (2013.01)

(56) References Cited

U.S. PATENT DOCUMENTS

2006/0047031 A1     3/2006    Cella et al.
2012/0059119 A1     3/2012    Bito et al.

OTHER PUBLICATIONS

Shibata et al. (Polymer Journal, 2011, 43, 916-922).*
"Drying Oil", The Columbia Encyclopedia, 6$^{th}$ ed.*
Mehta et al. Ind. Eng. Chem. Res. 2016, 55, 11727-11735.*
Hong, et al., Biopolymers from Vegetable Oils via Catalyst and Solvent Free "Click" Chemistry: Effects of Cross-Linking Density, Biomacromolecules 2012, vol. 13, pp. 261-266, p. 261.
Wang, A., Molecular Approach to the Synthesis of Novel Polyimides, Chinese Journal of Polymer Science, 1999, vol. 19, pp. 511-528.
Hirayama, et al., High-Performance Bio-based Thermosetting Resins Composed of Dehydrated Castor Oil and Bismaleimide; Journal of AppliedPolymer Science,vol. 114, 1033-1039 (2009).

* cited by examiner

SYNTHESIS OF CROSS-LINKED PLANT-OIL BASED POLYMERS USING BISMALEIMIDES AS CROSSLINKERS

CROSS-REFERENCE TO RELATED APPLICATIONS

This application claims priority from U.S. Provisional Patent Application No. 61/874,031 filed on Sep. 5, 2013, the contents of which are incorporated herein by reference.

STATEMENT REGARDING FEDERALLY SPONSORED RESEARCH OR DEVELOPMENT

This invention was made with government support under grant Nos. 7148582 and 1256123 awarded by the NSF. The government has certain rights in the invention.

FIELD OF THE INVENTION

One or more embodiments relate to a method of preparing a plant oil-based polymers by crosslinking a plant oil with a bismaleimide crosslinker and the resultant plant oil-based polymers.

BACKGROUND OF THE INVENTION

A broad array of markets utilize polymers including construction, automotive, aerospace and other consumer products. Presently, commercial resins are based on polyesters, vinyl esters, epoxies and urethanes that consist of chemicals with major concerns such as styrene, formaldehyde, epichlorohydrin, isocyanates, and bisphenol A (BPA). For example, bisphenol A is an endocrine disruptor mimicking the natural hormone estrogen and fools the body by stimulating unnecessary reactions, especially in infants and young children. The United States Food and Drug Administration have eliminated the use of the BPA in manufacturing of baby bottles, sippy cups and infant formula packaging. Lately, the global oil crisis has again brought the importance of polymers based on renewable resources into the forefront of research and industrial applications. The reasons for this paradigm shift include declining amounts and ever-increasing price of fossil fuels and the growing awareness of environment and human health.

Accordingly, there is a need to produce polymers that do not suffer from all or some of these deficiencies.

SUMMARY OF THE INVENTION

A first embodiment provides a method of preparing a plant oil based polymer comprising heating a plant oil in the presence of a bismaleimide crosslinker in the substantial absence of a solvent to a temperature at or above the melting temperature of the bismaleimide crosslinker, where the bismaleimide crosslinker is defined by the formula

where $R^1$ is a divalent organic group.

A second embodiment provides a method as in the first where the method is performed in less than 5% solvent.

A third embodiment provides a method as in the either the first or second embodiment, where the method is performed in the absence of a solvent.

A forth embodiment provides a method as in any of the first through third embodiments, where the plant oil in the presence of a bismaleimide crosslinker is heated to a temperature at or above 130° C.

A fifth embodiment provides a method as in any of the first through forth embodiments, where the plant oil in the presence of a bismaleimide crosslinker is heated to a temperature at or above 150° C.

A sixth embodiment provides a method as in any of the first through fifth embodiments, where at least 22% maleimine groups of the bismaleimide crosslinker react with the plant oil through an ene reaction.

A seventh embodiment provides a method as in any of the first through sixth embodiments, where the plant oil is a fatty acid, fatty ester, glycerolipid or combination thereof.

An eighth embodiment provides a method as in any of the first through seventh embodiments, where the plant oil is a glycerolipid and the glycerolipid is a triglyceride.

A ninth embodiment provides a method as in any of the first through eighth embodiments, where the plant oil is selected from soybean oil, linseed oil, corn oil, cotton seed oil, palm oil, and peanut oil.

A tenth embodiment provides a method as in any of the first through ninth embodiments, where the bismaleimide crosslink is defined by the formula

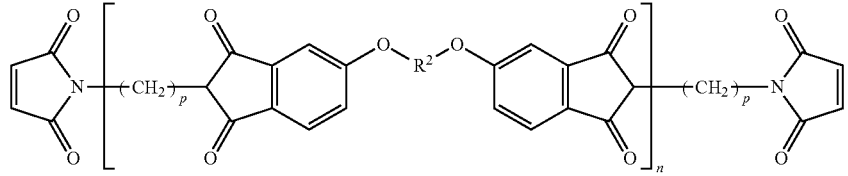

where $R^2$ is a divalent organic group and each p is individually 0 to about 36 units, and n is 1 to 10 units.

An eleventh embodiment provides a method as in any of the first through tenth embodiments, where the bismaleimide crosslink is defined by the formula

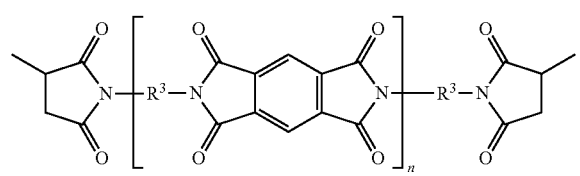

where each $R^3$ is individually a divalent organic group and each n is individually about 1 to about 10 units.

A twelfth embodiment provides a method as in any of the first through eleventh embodiments, where the bismaleimide crosslink is selected from the group consisting of

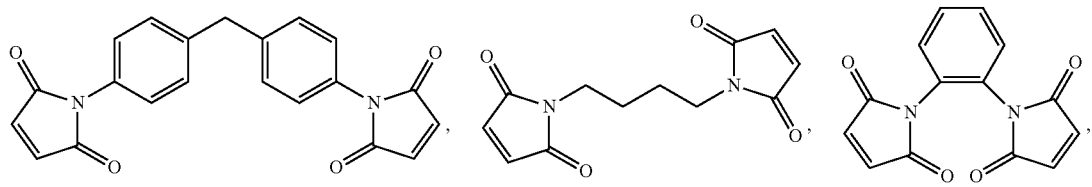

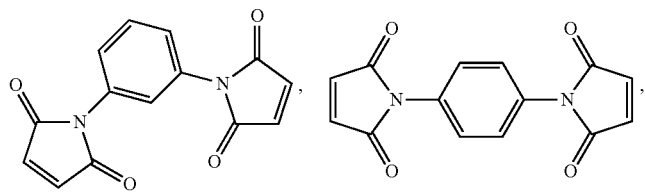

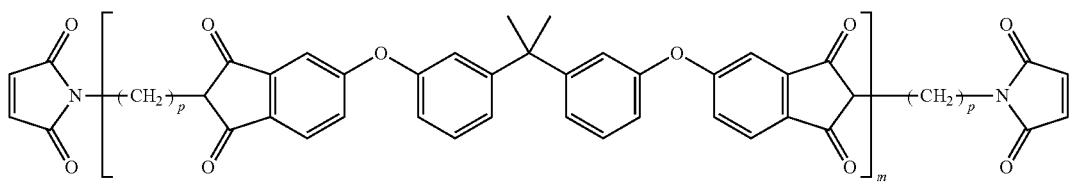

where each p is individually about 0 to about 36 units, and

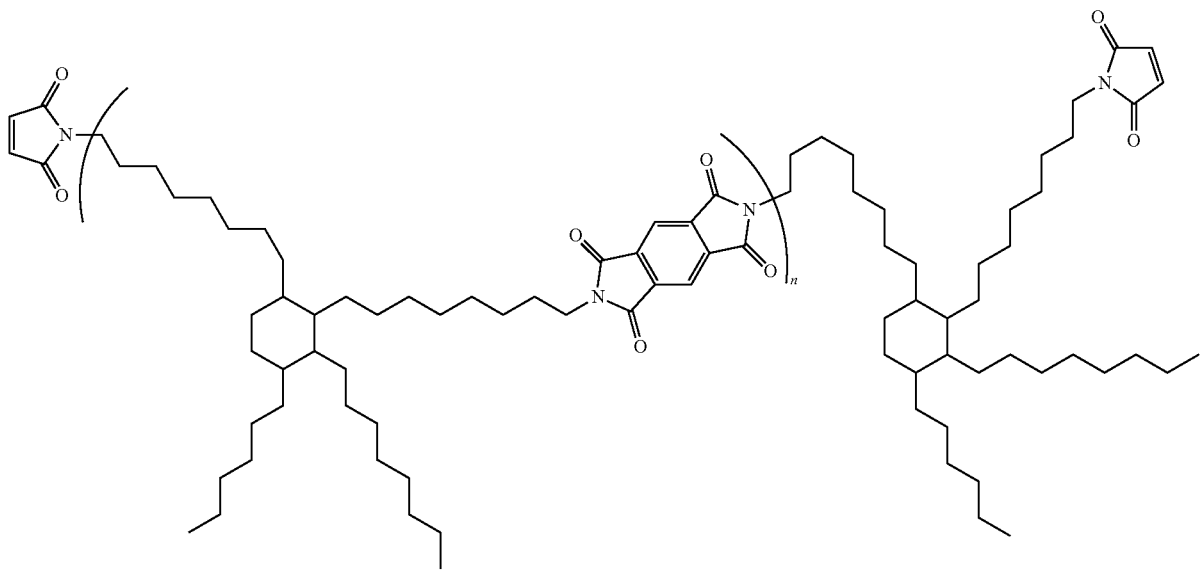

where n is 1 to 10.

A thirteenth embodiment provides a plant oil based polymer comprising a bismaleimide crosslinked plant oil, including a bismaleimide crosslink with a maleimide group bonded to the plant oil by a single bond, where the bismaleimide crosslink is defined by the formula II, formula III or a combination thereof, where formula II is defined by:

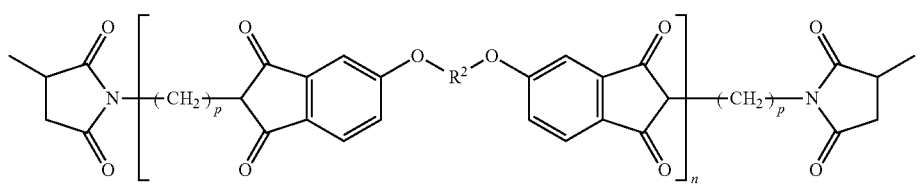

where $R^2$ is a divalent organic group, and each p is individually 0 to about 36 units, and formula III is defined by:

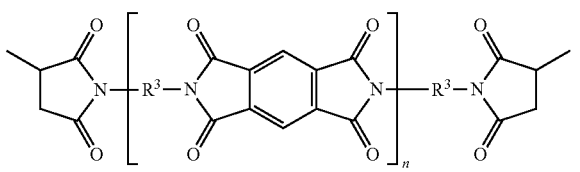

where each $R^3$ is individually a divalent organic group and each n is individually about 1 to about 10 units.

A fourteenth embodiment provides a plant oil based polymer as in the thirteenth embodiment, where at least 22% maleimine groups of the bismaleimide crosslinker react with the plant oil through an ene reaction.

A fifteenth embodiment provides a plant oil based polymer as in either of the thirteenth or fourteenth embodiment, where the plant oil is a fatty acid, fatty ester, glycerolipid or combination thereof.

A sixteenth embodiment provides a plant oil based polymer as in any of the thirteenth through fifteenth embodiments, where the plant oil is a glycerolipid and the glycerolipid is a triglyceride.

A seventeenth embodiment provides a plant oil based polymer as in any of the thirteenth through sixteenth embodiments, where the plant oil is selected from soybean oil, linseed oil, corn oil, cotton seed oil, palm oil, and peanut oil.

An eighteenth embodiment provides a composite material comprising a fiber, particulate filler, or combination thereof, and a bismaleimide crosslinked plant oil.

A nineteenth embodiment provides a composite material as in the eighteenth embodiment, where bismaleimide crosslinked plant oil includes a bismaleimide crosslink with a maleimide group bonded to the plant oil by a single bond.

A twentieth embodiment provides a composite material as in either the eighteenth or nineteenth embodiments, where the composite material further includes an inhibitor, accelerator, catalyst, pigment, dye, mold release agent, thixotrope, rheology modifier, compatibilizing agents, or combination thereof.

A twenty-first embodiment provides a method of preparing a plant oil based polymer comprising heating a reaction mixture consisting essentially of a plant oil in and a bismaleimide crosslinker to a temperature at or above the melting temperature of the bismaleimide crosslinker, where the bismaleimide crosslinker is defined by the formula

where $R^1$ is a divalent organic group.

DETAILED DESCRIPTION OF ILLUSTRATIVE EMBODIMENTS

Figure 1:
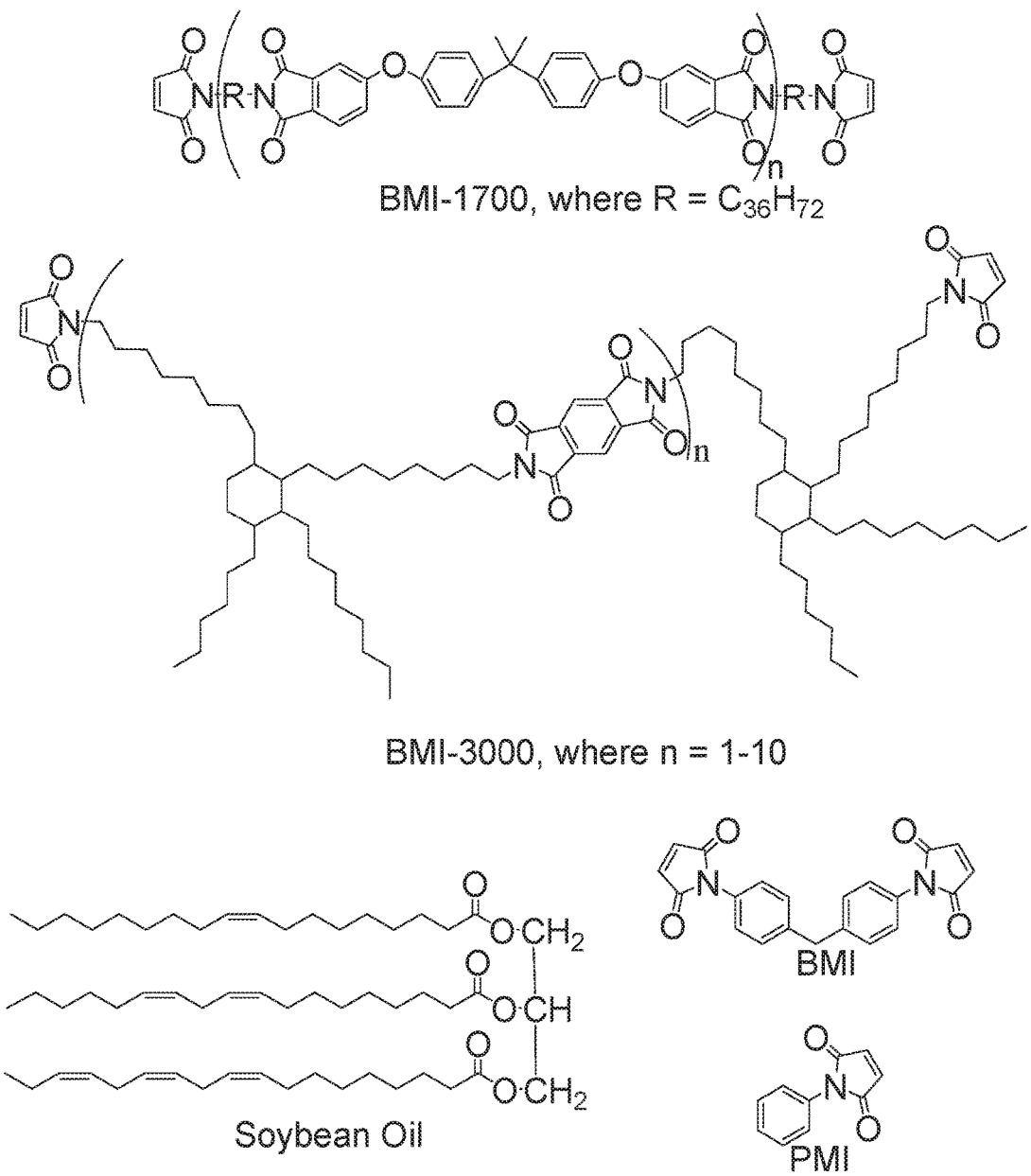
FIG. 1 provides the structures of the main components of Bismaleimide (BMI), N-Phenylmaleimide (PMI), BMI-1700, BMI-3000 and soybean oil.

Plant oils are bio-renewable and eco-friendly starting materials for polymers. One or more embodiments provide a method of preparing a plant oil-based polymers by cross-linking a plant oil with a bismaleimide crosslinker. The resultant plant oil-based polymers have advantageous thermal and mechanical properties for use in the fields of composites, adhesives and coatings In one or more embodiments, the method of preparing a plant oil based polymer comprises heating a plant oil in the presence of a bismaleimide crosslinker in the substantial absence of a solvent to a temperature at or above the melting temperature of the bismaleimide crosslinker.

Plant oils may be extracted from natural plant sources. Plant oils include fatty acids, fatty esters, glycerolipids and combinations thereof. Suitable glycerolipids include monoglycerides, diglycerides, and triglycerides. Suitable plant oils may be obtained from soybeans, linseeds, corn, cotton seeds, palms, and peanuts. Suitable plant oils include soybean oil, linseed oil, corn oil, cotton seed oil, palm oil, and peanut oil.

In one or more embodiments, the bismaleimide crosslinker may be defined by formula I:

where $R^1$ is a divalent organic group.

Suitable divalent organic groups for use in bismaleimide crosslinkers include hydrocarbylene groups with less than 30 carbon atoms, oligomeric groups or polymeric groups. The divalent organic groups may include cyclic and aromatic groups. The divalent organic groups may also include heteroatoms. Particularly useful heteroatoms include nitrogen and oxygen atoms, which may be used to connect multiple divalent organic groups to make a single, larger divalent organic group.

Some bismaleimide crosslinkers defined by formula I that include an $R^1$ group that is a short hydrocarbylene group have been found to be toxic, and thus their uses are limited. Advantageously, it has been found that bismaleimide crosslinkers defined by formula I with an $R^1$ group that is an oligomeric group or longer, do not suffer from high toxicity. This allows these crosslinkers to have broader applications. For instance, these groups may be used in bio-composites. In one or more embodiments, the bismaleimide crosslinker defined by formula has an $R^1$ group that is an oligomerized polyimide, which may be referred to herein as oligomerized polyimide crosslinker end-capped with maleic anhydride.

In one or more embodiments, when the bismaleimide crosslinker the is a oligomerized polyimide crosslinker end-capped with maleic anhydride the bismaleimide crosslinker may be defined by formula II:

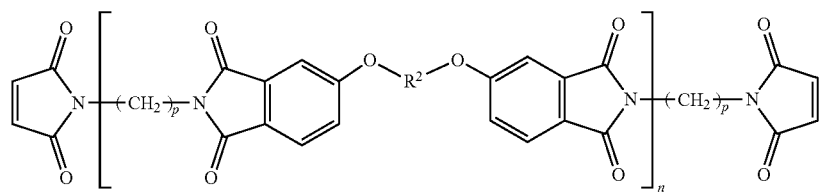

where $R^2$ is a divalent organic group, each p is individually 0 to about 36 units, and n is individually about 1 to about 10 units.

In one or more embodiments, when the bismaleimide crosslinker the is a oligomerized polyimide crosslinker end-capped with maleic anhydride the bismaleimide crosslinker may be defined by formula III:

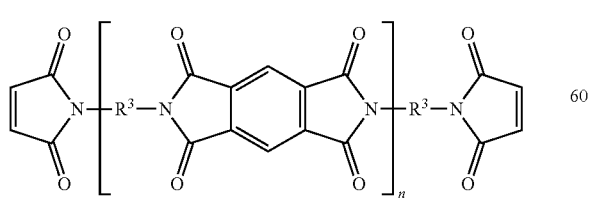

Where each $R^3$ is individually a divalent organic group and n is individually about 1 to about 10 units.

Specific examples of bismaleimide crosslinkers include:

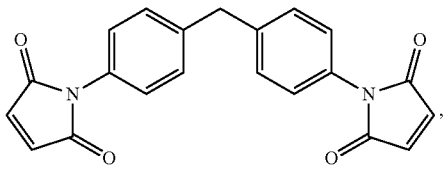

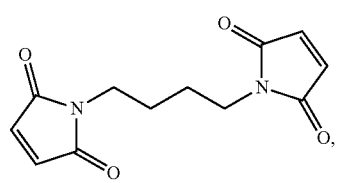

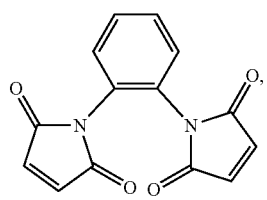

-continued

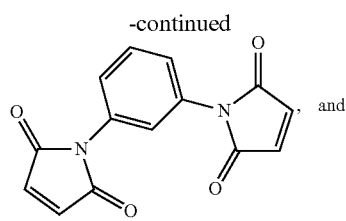
, and

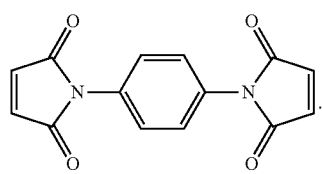
.

Specific examples of bismaleimide crosslinkers that are oligomerized polyimide crosslinkers end-capped with maleic anhydride include:

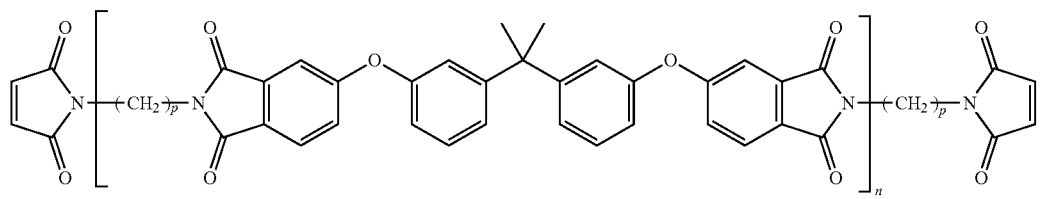

where each p is individually about 0 to about 36 units and n is about 1 to about 10, and

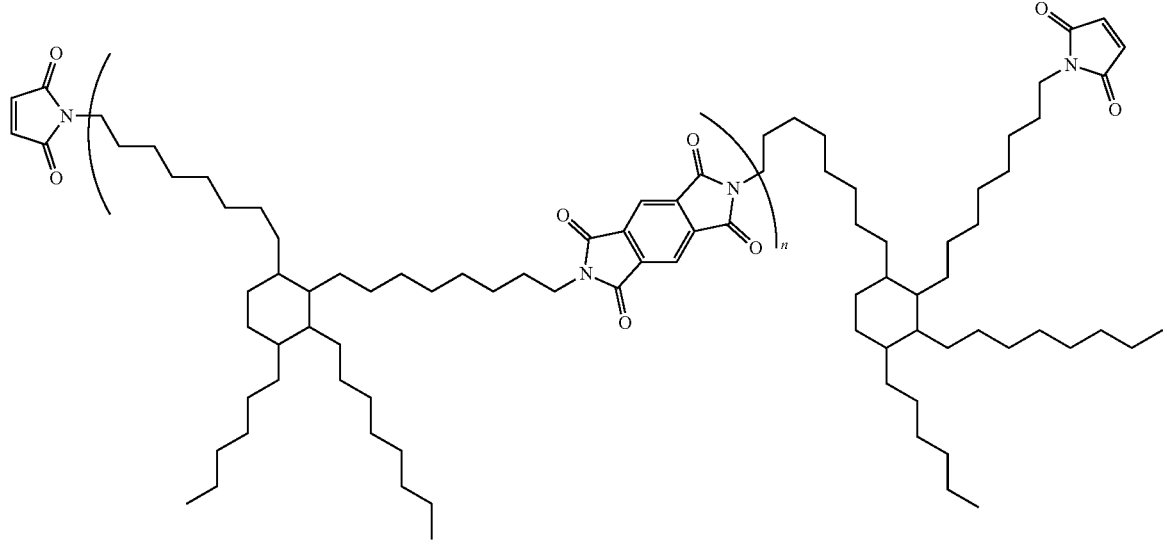

where n is about 1 to about 10.

As noted above, plant oil-based polymer may be prepared by heating a plant oil in the presence of a bismaleimide crosslinker at or above the melting temperature of the bismaleimide crosslinker. The melting temperature of the bismaleimide crosslinker may be determined by differential scanning calorimetry (DSC). In one or more embodiments, the bismaleimide crosslinker may be a liquid at room temperature, thus the heating of the plant oil and bismaleimide crosslinker mixture would be optional.

In one or more embodiments, the plant oil and bismaleimide crosslinker mixture may be heated to a temperature of at least 130° C., in other embodiments at least 140° C., and in other embodiments at least 150° C. In these or other embodiments, the plant oil and bismaleimide crosslinker mixture may be heated to a temperature of at most 220° C., in other embodiments at most 210° C., and in other embodiments at most 200° C. In these or other embodiments, the plant oil and bismaleimide crosslinker mixture may be heated to a temperature of about 130° C. to about 220° C., in other embodiments of about 140° C. to about 210° C., and in other embodiments at most of about 150° C. to about 200° C.

The amount of bismaleimide crosslinker used to produce a plant oil-based polymer may be described with reference to the amount of plant oil (i.e. moles of fatty acids, fatty esters, glycerolipids or combinations thereof). In one or more embodiments, the molar ratio of the bismaleimide crosslinker to plant oil may be about 0.15:1 to about 2:1, in other embodiments about 0.5:1 to about 1.5:1, in other embodiments about 0.8:1 to about 1.2:1, in other embodiments about 1:1.

As noted above, the plant oil-based polymer may be prepared in a process that is substantially solvent free. Substantially solvent free refers to a method that does not use a solvent as a diluent for the reactants. Or, in other words, the weight percentage of reactants is greater than the amount of solvent. In one or more embodiments, only the amount of solvent required to transfer the reactants is used. In one or more embodiments, the method is performed in less than 15% solvent, in other embodiments the method is performed in less than 5% solvent, in other embodiments the method is performed in the absence of a solvent.

In one or more embodiments, the plant oil-based polymer may be prepared in a process that includes heating a reaction mixture at or above the melting temperature of the bismaleimide crosslinker, the reaction mixture consisting essentially of a plant oil and a bismaleimide crosslinker A reaction mixture that consists essentially of a plant oil and a bismaleimide crosslinker does not include any other reactants or solvents in an amount that will materially alter the product of the reaction.

The bismaleimide crosslinker is capable of crosslinking the plant oil through an ene reaction.

Scheme 1: describes an exemplary ene reaction between ethyl oleate and N-phenylmaleimide.

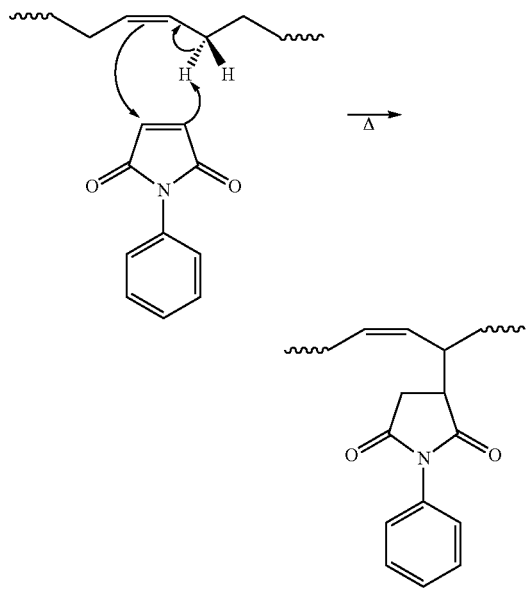

As can be seen from scheme 1, the ene reaction results in a maleimide group becoming a pendent succinimide group. Thus, when a maleimide group of the bismaleimide cross-linker undergoes an ene reaction the resultant succinimide group will be bonded to a plant oil by a single bond. In one or more embodiments, the plant oil-based polymer may be prepared in a process without the use of a radical polymerization inhibitor. Advantageously, the bismaleimide crosslinker may crosslink the plant oils through an ene reaction without the need for a radical polymerization inhibitor.

In one or more embodiments, at least 44% of the maleimine groups of the total maleimine groups of the bismaleimide crosslinker added react with the plant oil through an ene reaction, in other embodiments, at least 33% of the maleimine groups, and in still other embodiments at least 22% of the maleimine groups.

In one or more embodiments, the plant oil based polymer may be characterized by an advantageous storage modulus, which may be measured by dynamic mechanical analysis. In one or more embodiments, the plant oil based polymer is characterized by a storage modulus that is at least 0.5 MPa and in other embodiments at least 1.2 MPa. In these or other embodiments, the plant oil based polymer is characterized by a storage modulus that is at most 6 MPa and in other embodiments at most 4 MPa. In one or more embodiments, the plant oil based polymer may be characterized by a storage modulus that is from about 0.5 MPa to about 6 MPa. In certain embodiments the plant oil based polymer may be characterized by a storage modulus that is from about 0.5 MPa to about 6 MPa and in other embodiments from about 1.2 MPa to about 4 MPa.

In certain embodiments the plant oil based polymer may be characterized by a storage modulus that is from about 1.2 MPa to about 6 MPa. These or other embodiments may be useful as matrix resins for coatings and composite systems. In certain embodiments the plant oil based polymer may be characterized by a storage modulus that is from about 0.5 MPa to about 4 MPa. These or other embodiments may be useful in elastomer applications such as adhesives and soft touch coatings or impact protective coatings.

In one or more embodiments, a plant oil based polymer comprises a bismaleimide crosslinked plant oil, including a bismaleimide crosslink with a succinimide group bonded to the plant oil by a single bond.

In one or more embodiments, the bismaleimide crosslink of a plant oil based polymer may be defined by the formula

where $R^1$ is a divalent organic group.

In one or more embodiments, the bismaleimide crosslink of a plant oil based polymer may be defined by the formula

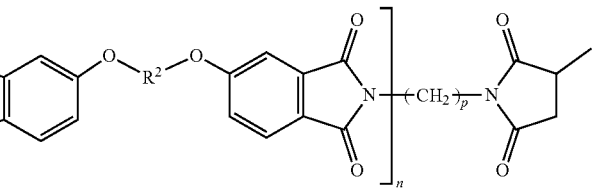

where $R^2$ is a divalent organic group, each p is individually 0 to about 36 units, and n is about 1 to about 10 units.

In one or more embodiments, the bismaleimide crosslink of a plant oil based polymer may be defined by the formula

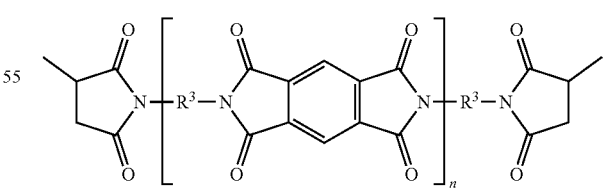

where each $R^3$ is individually a divalent organic group and each n is individually about 1 to about 10 units.

In one or more embodiments, the bismaleimide crosslink of a plant oil based polymer may be defined by one of the following formulas

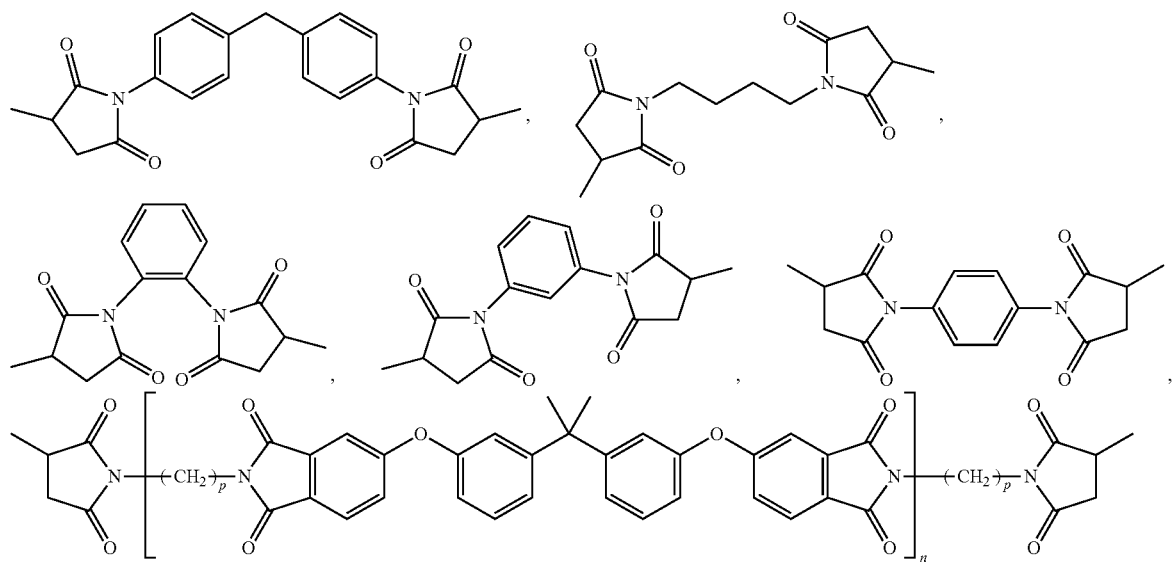

where each p is individually 0 to about 36 units an n is about 1 to about 10 unit, and

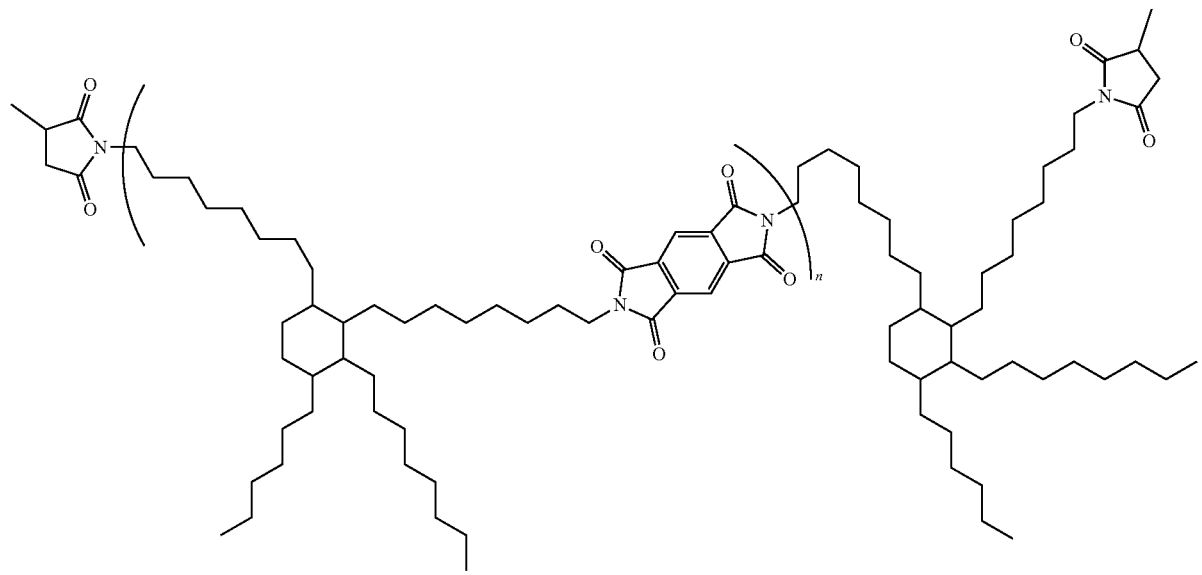

where n is about 1 to about 10 units.

In one or more embodiments, the plant oil based polymer may be used in a composite material. Composite materials are materials made from two or more materials. The materials may have different physical or chemical properties, that when combined, produce a material with characteristics different from the individual components. In one or more embodiments, the composite material may include a fiber, particulate filler, or combination thereof, and a bismaleimide crosslinked plant oil. A composite material that includes a plant oil based polymer may be referred to herein as a plant oil based polymer composite.

The amount of plant oil based polymer in the plant oil based polymer composite may be characterized by percent weight. In one or more embodiments, plant oil based polymer composites include about 10% to about 90% plant oil based polymer, in other embodiments about 15% to about 70% plant oil based polymer, and in still other embodiments about 20% to about 50% plant oil based polymer.

Fibers suitable for use in plant oil based polymer composites include short fibers and continuous fibers. In one or more embodiments, the fiber may be woven. In these or other embodiments, the woven fibers may be layered. Suitable fiber materials include, but are not limited to, glass, carbon, aramid and natural fibers. Natural fibers include, but are not limited to, wood pulp, cotton, hemp, bamboo, and kenaf.

In one or more embodiments, a short fiber has an average length of about 0.04 cm to about 7.5 cm, in other embodiments about 0.06 cm to about 5 cm, and in still other embodiments about 0.13 cm to about 2.5 cm.

Those skilled in the art will recognize that the length of a continuous fiber will vary according to the specific application. For example, windmill blades with wrapped reinforcements may use fibers that are greater than 300 m. In one or more embodiments, a continuous fiber has an average length greater than 10 cm, in other embodiments greater than 1 m, and in still other embodiments greater than 2 m. In these or other embodiments, a continuous fiber has an average length of about 10 cm to about 300 m, in other embodiments about 1 m to about 100 m, and in still other embodiments about 2 m to about 10 m.

The amount of fiber in the plant oil based polymer composite may be characterized by percent weight. In one or more embodiments, plant oil based polymer composites include about 0% to about 90% fiber, in other embodiments about 5% to about 70% fiber, and in still other about 15% to about 60% fiber.

Particles suitable for use in plant oil based polymer composites include mineral, silica, fly ash, or plant biomass particulate filler. Specific examples of plant biomass particulate filler include lignin, cellulose, protein, and combinations thereof. The particles may also be prepared from plant biomass derived particulate filler, which has been manipulated by chemical grafting, heat treatment, or another process to make it more hydrophobic and more suitable for use as a filler.

Particles may be characterized by the average diameter of the longest axis of the particle. In one or more embodiments, the average diameter of a particle is about 0.5 nm to about 0.3 cm, in other embodiments about 100 nm to about 500 um, and in still other embodiments about 2 um to about 30 um.

Suitable particle shapes include three dimensional structured particles, solid or hollow spheroids (shapes that are spherical or closely resemble a spherical shape), platelets, whiskers, microfibril, or nanofibril.

The amount of particles in the plant oil based polymer composite may be characterized by percent weight. In one or more embodiments, plant oil based polymer composites include about 0% to about 90% particles, in other embodiments about 5% to about 70% particles, and in still other embodiments about 15% to about 60% particles.

Optional components of plant oil based polymer composite include, but are not limited to, inhibitors, accelerators, catalyst, pigment or dyes, mold release agents, thixotropes, rheology modifiers, and compatibilizing agents.

Suitable methods for preparing a plant oil based polymer composite composite include, but are not limited to, bulk compounding, sheet compounding, injection and compression molding, laminate wet molding, solvent and hot melt impregnation, resin transfer molding, vacuum assist molding, bag or autoclave molding, and filament winding.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Materials

Oleic acid (Eastman Chemical Company, Pamolyn™ 100 FGK Kosher), Methyl Linoleate (Sigma Aldrich, ≥99% GC), Soybean Oil (Sigma Aldrich), Linseed Oil (Cargill, Supreme Grade), N-Phenylmaleimide (Sigma Aldrich, 97%), 1,3-Dimethyl-2-imidazolidinone (Aldrich, 98%), 1,1'-(Methylenedi-4,1-phenylene)bismaleimide (Sigma Aldrich, 95%), BMI-1700 (Designer Molecules), Ethanol (Sigma Aldrich, anhydrous, ≥99.5%), Oxalyl Chloride (Aldrich, 98%) and Pyridine were used as received. Ethyl Oleate was synthesized and purified according to a described procedure.[1] Reagent grade methylene chloride ($CH_2Cl_2$) was dried by distillation from calcium hydride under $N_2$.

Techniques

All reactions and polymerizations were conducted under a $N_2$ atmosphere using a Schlenk line unless noted otherwise. $^1H$ and $^{13}C$ NMR spectra (δ, ppm) were recorded on either a Varian Mercury 300 or Varian NMRS 500 (300 MHz or 500 MHz) instruments. Unless noted otherwise, all spectra were recorded in $CDCl_3$, and the resonances were measured relative to residual solvent resonances and referenced to tetramethylsilane (0.00 ppm). Thermal analysis was performed on a Perkin Elmer Pyris 1 differential scanning calorimeter. Heating and cooling rates were 10° C./min. Transition temperatures were calibrated using indium and tin standards; enthalpy was calibrated using an indium standard. The 5% weight loss temperature was measured on a thermogravimetric analyzer TA Instrument Model Q500 TGA in a nitrogen atmosphere at a heating rate of 10° C./min. The tan delta and storage modulus values were obtained on a Rheometric Scientific DMTA IV instrument using a specimen of dimensions 1 cm×5 cm×0.14 cm.

Synthesis of Ethyl Oleate

To a chilled solution of oleic acid (5.0 mL, 16 mmol) in methylene chloride (23 mL) was added drop wise oxalyl chloride (2.9 g, 24 mmol) for four minutes. Reaction warmed to room temperature and stirred for 3 hours. Then added drop wise ethanol (9.0 mL) and pyridine (9.0 mL), while cooling the reaction mixture in dry-ice bath. Reaction was stirred at room temperature for 15½ hours and diluted with 100 ml methylene chloride and organic phase was washed three times with saturated aqueous solution of sodium bicarbonate (25 mL each), twice with saturated aqueous solution of ammonium chloride (25 mL each) and four times with water (50 mL each). The combined organic phase was dried over $MgSO_4$ and filtered using glass frit. After filtration, solvent was removed under reduced pressure and concentrated further using vacuum and heat to obtain yellow oil. The yellow oil was purified by column chromatography using silica gel as the stationary phase and Hexanes:$Et_2O$ (5:1 v/v) as the eluent to yield 2.72 g (55.5%) of ethyl oleate as colorless oil. $^1H$ NMR: 0.88 (t, $CH_3$, J=6.0 Hz), 1.22-1.31(m, $(CH_2)_{10}$), 1.25 (m, $COOCH_2CH_3$), 1.60-1.64 (m, $COCH_2CH_2$), 1.99-2.02 (dt, $CH_2CH=CHCH_2$, J=12 Hz, 6 Hz), 2.28 (t, $COCH_2$, J=7.5 Hz), 4.11 (q, $COOCH_2CH_3$, J=9.0 Hz), 5.32-5.37 (m, CH=CH). $^{13}C$ NMR: 14.14 ($CH_3$), 14.31 ($COOCH_2CH_3$), 22.73-34.44 $(CH_2)_{13}$, 60.16 ($COOCH_2CH_3$), 129.80-130.04 (CH=CH), 173.88 ($COOCH_2CH_3$).

Polymerization

In a typical procedure, mixture of fatty acid, fatty acid esters or triglycerides (1.0 equivalent) and the crosslinker (2.0 equivalent) was stirred for 30 min at 150° C. The reaction product obtained was purified using a Soxhlet extraction technique with methylene chloride as the solvent and dried under vacuum to give yellow cross-linked product.

Results and Discussion

Characterization of Ethyl Oleate.

Ethyl oleate was reasoned as a model compound to unravel the reactions occurring with the more complex triglyceride structure. In the $^1H$-NMR spectrum of the ethyl oleate, the methyne proton signal assigned $H_{9-10}$ is observed at 5.34 ppm, belongs to the olefinic protons of the fatty ester.

The most characteristic peak $H_{2'}$ in the spectrum is at 4.11 ppm corresponding to the two hydrogen of the methylene in the ester group. The methyl proton signal of $H_{3'}$ was observed at 1.25 ppm, which overlaps with the backbone methylene resonances.

Characterization of the Reaction Products of Ethyl Oleate (EO) and N-Phenylmaleimide (PMI).

Figure 2:
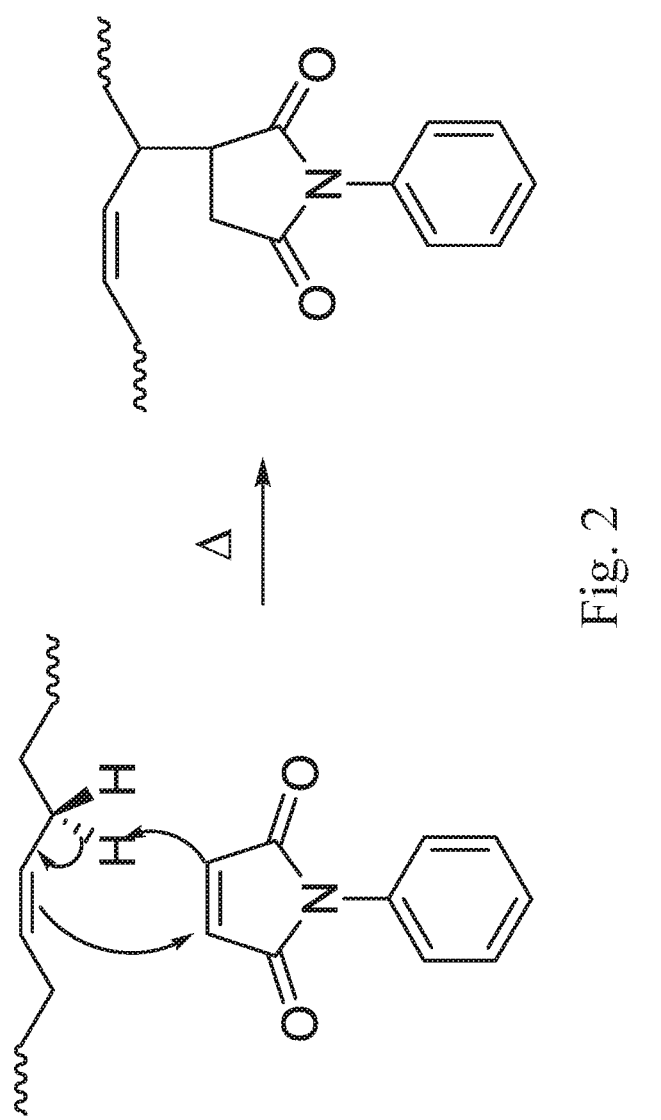
FIG. 2 provides a scheme of an ene reaction product between ethyl oleate and N-phenylmaleimide.

Detailed understanding of the ene reaction chemistry was achieved by studying the reaction between SBO and PMI. Plausible reaction mechanism between SBO and PMI is highlighted in FIG. 2. The product obtained by the reactions of SBO and PMI with 1/1 stoichiometric ratio at 150° C. for 16 h were analyzed by $^1$H NMR spectroscopy.

From $^1$H NMR spectrum of soybean oil the number of olefins (CH=CH) per triglycerides (I) was evaluated to be approximately 4.62 using integral values (IA) in equation: I=[9(IA of 5.2-5.4 ppm)–(IA of 0.8-1.0 ppm)]/[2(IA of 0.8-1.0 ppm)]. Based on the fact that terminal methyl groups of soybean oil do not change before and after reaction, number of olefins per triglyceride classified into four categories was determined using IA of various proton signals of the reaction product of SBO and PMI. There were no conjugated moiety resonances observed at 6.35-5.52 ppm in the starting material and hence in we did observe any visible resonances belonging to the Diels Alder reaction product in the spectrum region, 5.92-5.82 ppm. The methylene proton signals ($CH_2$-C=O) formed by ene reaction was observed at 3.03 ppm. The number of olefins of reaction product (II) was lower than the number of olefins in the starting material (I). It was calculated to be 3.285. The number of olefins created by ene reaction (III) is equal to the number of ene-reacted maleimide groups. Based on calculation, that number was found to be 0.995. Hence, the percent of maleimide group reacted based on the values obtained from IA is about 22%. This value would certainly increase with increasing amounts of PMI.

Characterization and Properties of the Cross-Linked Products with BMI and BMI-1700.

Commercialization of BMI is hindered due to its toxicity. It has been found that oligomerized polyimide cross-linkers end-capped with maleic anhydride do not suffer from the toxicity concerns of BMI and may be used as the enophile to obtain commercially viable bio-composites. Although the substrates (ene), BMI and BMI-1700 are soluble in chloroform, methylene chloride, dimethyl sulfoxide, tetrahydrofuran and methanol, all the cross-linked products were insoluble to their solvents and other common organic solvents, indicating that the cross-linked products have undoubtedly cured. The polymers were prepared by curing at 150° C. for 30 min with ratio of monomer to crosslinker 1:1 and 1:2. Table I summaries selected samples used in the study and characterization of the polymer product.

TABLE I

Selected Samples from the reaction with cross-linkers

| Entry No. | Ene:Enophile | Molar Ratios | T (° C.) | Comments |
|---|---|---|---|---|
| 1 | Oleic Acid:BMI | 1:1 | 150 | Neat |
| 2 | Ethyl Oleate:BMI | 1:1 | 150 | Neat |
| 3 | Methyl Linoleate:BMI | 1:1 | 150 | Neat |
| 4 | Soybean Oil:BMI | 1:1/1:2 | 150 | Neat |
| 5 | Linseed Oil:BMI | 1:1/1:2 | 150 | Neat |
| 6 | Soybean Oil:BMI-1700 | 1:1/1:2 | 150 | Neat |
| 7 | Linseed Oil:BMI-1700 | 1:1/1:2 | 150 | Neat |

Figure 3:
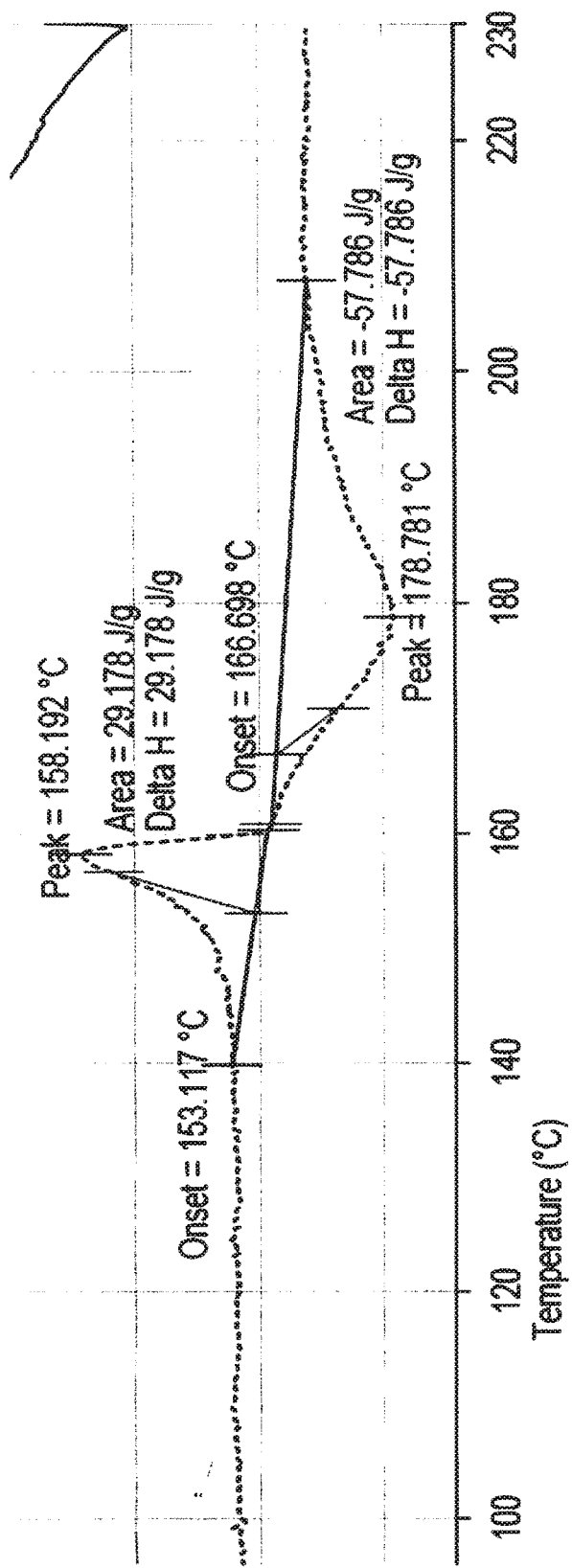
FIG. 3 provides a chart of a first DSC heating scan (10° C./min) exhibiting a cross-linking temperature between soybean oil and BMI.

FIG. 3 shows a DSC heating scan of the crosslinking reaction between soybean oil and BMI. Curing was achieved during the first heat cycle. The endothermic curve corresponding to a peak temperature of 158.2° C. represents the melting point of the BMI, which follows with an exothermic curve of reaction between the soybean oil and BMI. The peak reaction temperature of 178.8° C. is proof of the ene reaction occurring. Table 2 summaries the glass transition temperature ($T_1$) and thermal decomposition temperature of the various cross-linked products.

TABLE II

The $T_g$, $T_{5\%}$ and G' for samples made from triglyceride oils

| Sample | Molar Ratios | $T_g$ (° C.) [DMA] | $T_{5\%}$ (° C.) [TGA] | G' (GPa) [DMA] |
|---|---|---|---|---|
| SBO/BMI | 1:2 | 153 | 334 | 2.13 |
| LO/BMI | 1:2 | 147 | 332 | 3.21 |
| SBO/BMI-1700 | 1:2 | | 366 | |

$T_{5\%}$ means 5% weight loss temperature.
G' is the storage modulus expressed in GPa.

What is claimed is:

1. A method of preparing a plant oil based polymer comprising heating a plant oil in the presence of a bismaleimide crosslinker in the substantial absence of a solvent at a temperature of 130° C. to 200° C. to thereby form a plant oil based polymer in one step, where the bismaleimide crosslinker is defined by the formula

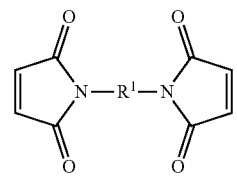

where $R^1$ is a divalent organic group.

2. The method of claim 1, where the method is performed in less than 5% solvent.

3. The method of claim 1, where the method is performed in the absence of a solvent.

4. The method of claim 1, where at least 22% maleimine groups of the bismaleimide crosslinker react with the plant oil through an ene reaction.

5. The method of claim 1, where the plant oil is a fatty acid, fatty ester, glycerolipid or combination thereof.

6. The method of claim 1, where the plant oil is a glycerolipid and the glycerolipid is a triglyceride.

7. The method of claim 1, where the plant oil is selected from soybean oil, linseed oil, corn oil, cotton seed oil, palm oil, and peanut oil.

8. The method of claim 1, where the bismaleimide crosslinker is defined by the formula

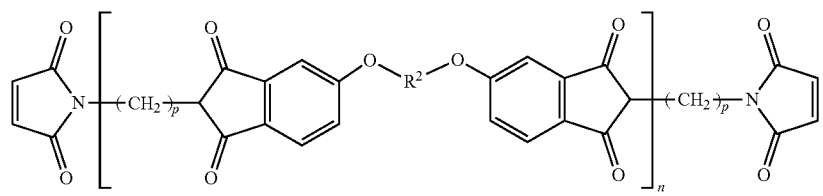

where $R^2$ is a divalent organic group and each p is individually 0 to about 36 units, and n is about 1 to about 10 units.

9. The method of claim 1, where the bismaleimide crosslink is defined by the formula

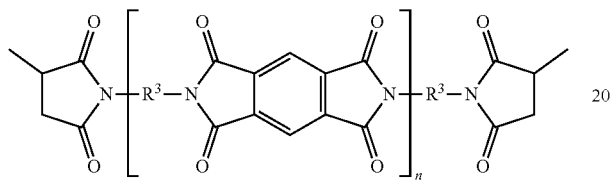

where each $R^3$ is individually a divalent organic group and each n is individually about 1 to about 10 units.

10. The method of claim 1, where the bismaleimide crosslinker is selected from the group consisting of

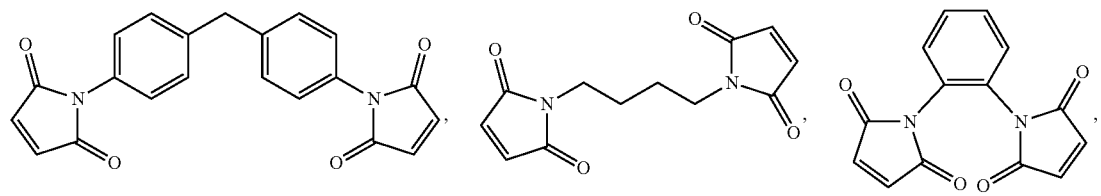

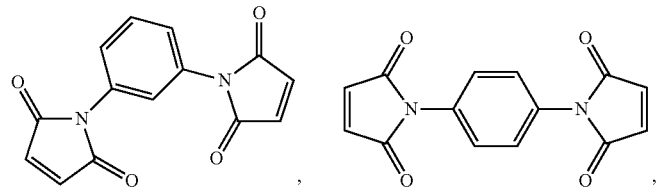

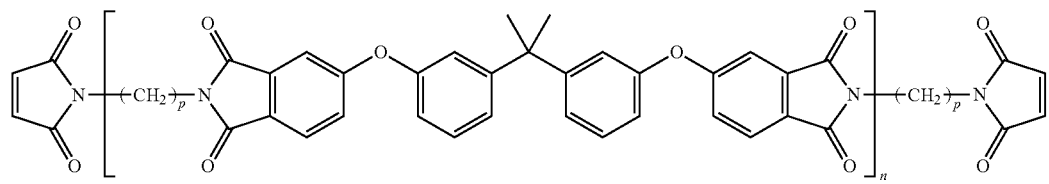

where each p is individually 0 to about 36 units, and

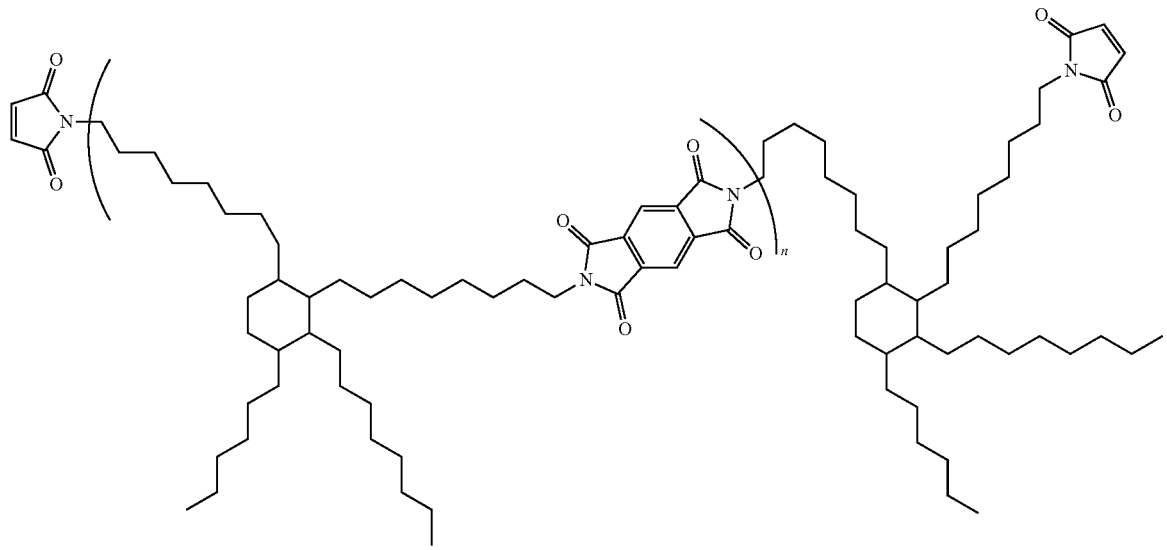

where n is about 1 to about 10.

11. A method of preparing a plant oil based polymer comprising heating a reaction mixture consisting essentially of a plant oil and a bismaleimide crosslinker at a temperature of 130° C. to 200° C. to thereby form a plant oil based polymer in one step, where the bismaleimide crosslinker is defined by the formula

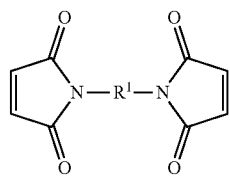

where $R^1$ is a divalent organic group.

12. A method of preparing a plant oil based polymer comprising:
(i) preparing a reaction mixture that is essentially solvent free by combining a plant oil and a bismaleimide crosslinker;
(ii) heating said reaction mixture at a temperature of 130° C. to 200° C. until a crosslinked polymer is formed, where the bismaleimide crosslinker is defined by the formula

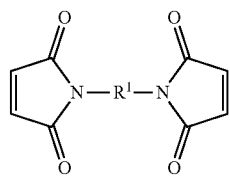

where $R^1$ is a divalent organic group.

13. A method of preparing a plant oil based polymer comprising
heating a plant oil in the presence of a bismaleimide crosslinker in the substantial absence of a solvent to a temperature at or above the melting temperature of the bismaleimide crosslinker, where the bismaleimide crosslinker is defined by the formula

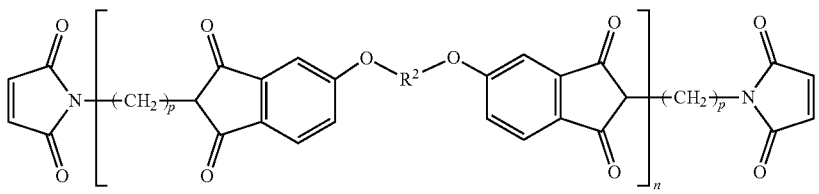

where $R^2$ is a divalent organic group and each p is individually 0 to about 36 units, and n is about 1 to about 10 units.

14. A method of preparing a plant oil based polymer comprising heating a plant oil in the presence of a bismaleimide crosslinker in the substantial absence of a solvent to a temperature at or above the melting temperature of the bismaleimide crosslinker, where the bismaleimide crosslink is defined by the formula

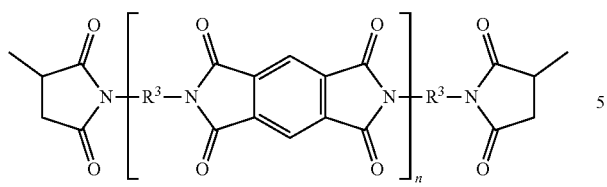
where each $R^3$ is individually a divalent organic group and each n is individually about 1 to about 10 units.
* * * * *